US006984208B2

(12) United States Patent
Zheng

(10) Patent No.: US 6,984,208 B2
(45) Date of Patent: Jan. 10, 2006

(54) METHOD AND APPARATUS FOR SENSING BODY GESTURE, POSTURE AND MOVEMENT

(75) Inventor: Yongping Zheng, Kowloon (HK)

(73) Assignee: The Hong Kong Polytechnic University, Kowloon (HK)

( * ) Notice: Subject to any disclaimer, the term of this patent is extended or adjusted under 35 U.S.C. 154(b) by 166 days.

(21) Appl. No.: 10/209,642

(22) Filed: Aug. 1, 2002

(65) Prior Publication Data

US 2004/0024312 A1 Feb. 5, 2004

(51) Int. Cl.
 *A61B 8/00* (2006.01)

(52) U.S. Cl. ....................... 600/438; 600/595

(58) Field of Classification Search ......... 600/437–471, 600/588, 592, 594–595
 See application file for complete search history.

(56) References Cited

U.S. PATENT DOCUMENTS

| | | | | | |
|---|---|---|---|---|---|
| 4,314,379 | A | * | 2/1982 | Tanie et al. ...................... 3/1.1 |
| 4,809,702 | A | * | 3/1989 | Fabbri et al. ................ 600/454 |
| 4,979,124 | A | * | 12/1990 | Sachse et al. .................. 73/587 |
| 5,385,147 | A | * | 1/1995 | Anderson et al. ............ 600/458 |
| 5,433,201 | A | * | 7/1995 | Manthey ...................... 600/438 |
| 5,469,861 | A | * | 11/1995 | Piscopo et al. .............. 340/573 |
| 5,474,070 | A | * | 12/1995 | Ophir et al. ................. 600/437 |
| 5,524,626 | A | * | 6/1996 | Liu .............................. 600/442 |
| 5,596,993 | A | * | 1/1997 | Oriol et al. ................... 128/898 |
| 5,598,845 | A | * | 2/1997 | Chandraratna et al. ..... 600/459 |
| 5,701,897 | A | * | 12/1997 | Sano ........................... 600/453 |
| 5,714,698 | A | | 2/1998 | Tokioka et al. |
| 5,810,731 | A | * | 9/1998 | Sarvazyan et al. .......... 600/438 |
| 5,957,846 | A | * | 9/1999 | Chiang et al. ............... 600/447 |
| 6,007,489 | A | * | 12/1999 | Yost et al. ................... 600/449 |
| 6,099,471 | A | * | 8/2000 | Torp et al. ................... 600/438 |
| 6,104,379 | A | | 8/2000 | Petrich et al. |
| 6,106,463 | A | * | 8/2000 | Wilk ........................... 600/437 |
| 6,106,464 | A | * | 8/2000 | Bass et al. ................... 600/439 |
| 6,128,004 | A | | 10/2000 | McDowall et al. |
| 6,167,145 | A | * | 12/2000 | Foley et al. ................. 382/128 |
| 6,185,451 | B1 | | 2/2001 | Richardson et al. |
| 6,238,342 | B1 | * | 5/2001 | Feleppa et al. ............. 600/437 |
| 6,319,201 | B1 | * | 11/2001 | Wilk ........................... 600/437 |
| 2001/0051766 | A1 | * | 12/2001 | Gazdzinski ................. 600/309 |

OTHER PUBLICATIONS

Abboudi et al., "A Biomimetic controller for a Multifinger Prosthesis", IEEE Transactions on Rehabilitation Engineering, vol. 7, No. 2, Jun. 1999, pp. 121–129.
Kenney et al., "Dimensional change in muscle as a control signal for powered upper limb prostheses: a pilot study", Medical Engineering & Physics, vol. 21 (1999) pp. 589–597.

* cited by examiner

*Primary Examiner*—Francis J. Jaworski
(74) *Attorney, Agent, or Firm*—Leydig, Voit & Mayer, Ltd.

(57) ABSTRACT

A method for indirectly assessing the gesture, posture or movement of a body part of a person includes transmitting an ultrasound signal into the soft tissue, particularly the muscle, of body part and manipulating the reflected ultrasound signal to obtain parameter data. The parameter data is compared to reference information to obtain gesture, posture or movement information for the body part. Apparatus includes an ultrasound transmitter and receiver for transmitting, a signal processor, and a processor for storing reference information and determining gesture, posture or movement information for the body part.

22 Claims, 2 Drawing Sheets

METHOD AND APPARATUS FOR SENSING BODY GESTURE, POSTURE AND MOVEMENT

BACKGROUND TO THE INVENTION

1. Field of the Invention

The present invention relates to a method and apparatus for sensing the gesture, posture and movement (GPM) of the head, limbs, limb parts and other parts of the body.

2. Background Information

Current techniques for tracking, or establishing, the gesture, posture or movement of a body or body part can be summarized into two categories. The first category comprises those systems that utilize external reference sources such as magnetic waves reflected off the body to detect the position or movement of body parts. The second category comprises those devices that use sensors on the body; such as gyroscopes, accelerometers, potentiometers, hand-gloves and jackets; for detecting the position and dynamic motion of a body part.

The problem with known systems is that they require some external reference to the body, and/or require a large and awkward attachment to the body part in order to perform their task.

SUMMARY OF THE INVENTION

It is an object of the present invention to provide a method and apparatus for determining the gesture, posture and movement of a body part of a person that is small and causes less discomfort to the person.

It is yet a further object of the present invention to provide a method and apparatus that overcomes or ameliorates problems with known systems, or that at least provides the public with a useful alternative.

According to a first aspect of the invention there is provided a method for indirectly assessing the gesture, posture or movement of a body part of a person including:
- applying an ultrasound transmitter and receiver to a body part to be monitored,
- using the transmitter to transmit an ultrasound signal into the body part and receiving a reflected and/or scattered ultrasound signal at the receiver,
- manipulating the reflected and/or scattered ultrasound signal to obtain parameter data, and
- comparing the parameter data to reference information to obtain gesture or posture information for the body part.

According to a second aspect of the invention there is provided a method for indirectly assessing the gesture, posture or movement of a body part of a person including:
- applying an ultrasound transducer or transducer array to a body part to be monitored,
- using a transmitter to transmit an ultrasound signal into the body part and receiving a reflected and/or scattered ultrasound signal at the receiver via the ultrasound transducer or transducer array,
- manipulating the reflected and/or scattered ultrasound signal to obtain parameter data, and comparing the parameter data to reference information to obtain gesture or posture information for the body part.

Preferably, the method includes analysing changes in gesture or posture to determine movement information for the body part.

Preferably, the ultrasound signal is transmitted into muscle tissue used to manipulate the body part.

Preferably, the ultrasound signal is transmitted into tendon tissue linking muscle tissue and the body part.

Preferably, parameter information is one or more of amplitude, phase, flight-time, frequency spectrum and waveform pattern of the reflected signal.

Preferably, the method includes an initial training step for obtaining reference information, the training step including:
- using the transmitter to transmit one or more training signals into the body part and receiving reflected and/or scattered training signals at the receiver via the ultrasound transducer or transducer array,
- manipulating the reflected and/or scattered training signals to obtain training parameter data, wherein the training parameter data includes one or more of amplitude, phase, flight-time, frequency spectrum and waveform pattern of the reflected training signals, and
- storing the training parameter data as reference information.

According to a third aspect of the invention there is provided a method for indirectly assessing the gesture, posture or movement of a body part of a person including:
- applying an ultrasound transducer or transducer array to a body part to be monitored,
- using a transmitter to transmit ultrasound signals into the body part and receiving reflected and/or scattered ultrasound signals at the receiver,
- manipulating the reflected and/or scattered ultrasound signals to obtain a plurality of parameter data, and
- comparing changes in the parameter data to determine movement information for the body part.

According to a forth aspect of the invention there is provided apparatus for indirectly assessing the gesture, posture or movement of a body part of a person including:
- an ultrasound transducer or transducer array for attaching to a body part to be monitored,
- an ultrasound transmitter and receiver for transmitting an ultrasound signal into the body part and receiving a reflected and/or scattered ultrasound signal,
- a signal processor for manipulating the reflected ultrasound signal to obtain parameter information, and
- a processor for storing reference information and comparing the parameter information to said reference information to determine gesture, posture or movement information for the body part.

Preferably, the apparatus further includes a data collector for receiving and storing the reflected and/or scattered signal and/or parameter information.

Preferably, the ultrasound transmitter is adapted and arranged to transmit the ultrasound signal into muscle tissue, and the receiver is adapted and arranged to receive the reflected and/or scattered ultrasound signals for the muscle tissue via the ultrasound transducer or transducer array.

Preferably, at least the processor is implemented on a computer, the computer including a display to graphically illustrate the gesture, posture or movement information for the body part.

Preferably, the ultrasound transducer, transmitter and receiver, signal processor, and the processor are integrated into a compact unit that can be worn on the body part.

Preferably, the ultrasound transducer, transmitter and receiver, signal processor, and the processor are integrated into a compact unit that can be embedded in the body part.

Preferably, the ultrasound transducer is integrated with other types of sensors for monitoring the gesture, posture, and movement of the body part.

Preferably, the ultrasound transducer has a flat shape.

Preferably, the ultrasound transducer is attached on the body surface by adhesive materials on the transducer surface.

Preferably, the ultrasound transducer is embedded in the inner surfaces of a prosthesis socket.

Preferably, the ultrasound transducer array is arranged on a flexible substance.

According to a fifth aspect of the invention there is provided a method for indirectly assessing the gesture, posture or movement of a body part of a person including:

applying an ultrasound transmitter and receiver to a body part to be monitored, applying a tissue stimulator on the body part to manipulate muscle and/or tendon tissue of the body part, using the transmitter to transmit a detecting ultrasound signal into the body part and receiving a reflected and/or scattered ultrasound signal at the receiver, processing the reflected and/or scattered ultrasound signal to obtain the stiffness information of the muscle and/or tendon tissue, and comparing the stiffness information to reference information to obtain gesture or posture information for the body part.

According to a sixth aspect of the invention there is provided apparatus for indirectly assessing the gesture, posture or movement of a body part of a person including:

an ultrasound transducer or transducer array for attaching to a body part to be monitored, an ultrasound transmitter and receiver for transmitting a detecting ultrasound signal into the body part and receiving a reflected and/or scattered ultrasound signal, a tissue stimulator for manipulating muscle and/or tendon tissues of the body part, a signal processor for processing the reflected ultrasound signal to obtain the tissue stiffness information, and a processor for storing reference information and comparing the tissue stiffness information to said reference information to determine gesture, posture or movement information for the body part.

Preferably, the tissue stimulator is a compressor for loading and unloading the muscle and/or tendon tissues in a static way.

Preferably, the tissue stimulator is a low frequency vibrator for vibrating the muscle and/or tendon tissues.

Preferably, the tissue stimulator is a second ultrasound transmitter for transmitting a stimulating ultrasound beam into the muscle and/or tendon tissues.

Further aspects of the invention will become apparent from the following description, which is given by way of example only.

BRIEF DESCRIPTION OF THE DRAWINGS

Embodiments of the invention will now be described with reference to the accompanying drawings in which.

DESCRIPTION OF THE PREFERRED EMBODIMENTS

Figure 1:
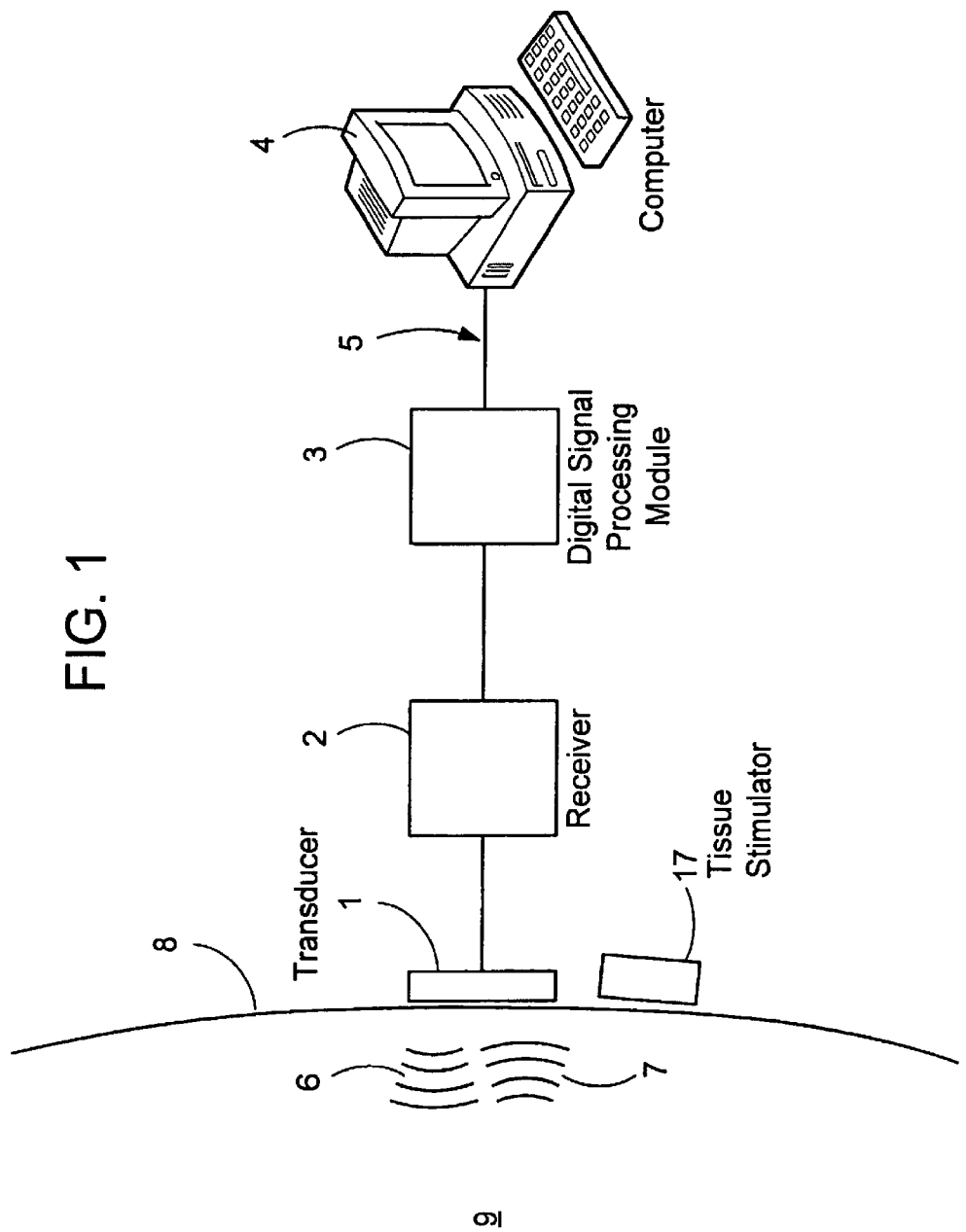
FIG. 1 illustrates a block diagram of apparatus according to a preferred embodiment of the invention.

Referring to FIG. 1, single or multiple ultrasound transducers 1 are attached on the skin surface 8 to transmit ultrasound waves 6 into the soft tissues 9 of a part of the body. One transducer 1 can be used for transmitting and/or receiving ultrasound signals 6,7. Multiple transducers 1 can be used to transmit or receive ultrasound signals 6,7 simultaneously. The ultrasound signals 6 are reflected and/or scattered from the various tissue interfaces and inside various tissues 9. These reflected and/or scattered ultrasound signals 7 are received, digitized, and processed to obtain various parameters of the signal. The various parameters are related to the dimension, position, angle and/or strength of the muscle, tendon or other tissues and are further related to the gesture and/or posture of the body part associated with the soft tissue. Different gestures and postures will result in different ultrasound reflected and/or scattered signals 7. Thus signal parameters are compared to a table of reference information to determine the gesture and/or posture of the body part.

The ultrasound signals are continuously recorded and analyzed to detect the changes in the soft tissues, particularly the muscles. The movement of the body parts can then be determined by analysing the information of the soft tissue changes, that is to say the changes in gesture and posture. The changes of muscles, tendons or other soft tissues can happen perpendicularly to the skin surface, or along the skin surface, which can be detected using multiple transducers or a transducer array aligned along the direction of the changes.

The parameters of ultrasound signals for detecting those differences may include amplitude, phase, flight-time, frequency spectrum, waveform pattern and their combinations. Various known signal processing techniques can be used to extract the parameter information.

The preferred embodiment of an apparatus for use in the invention includes an ultrasound transducer 1, an ultrasound transmitter and receiver 2, and digital signal processing module 3. These interface with a computer 4, which comprises a data collection module and a processor for storing reference information and comparing signal parameters to determine gesture and posture. The processor also analyses changes in gesture and posture to determine movement of the body part.

Alternative embodiments of the invention include two or more transducers located perpendicular to and/or along the skin surface.

In the preferred embodiment the computer 4 includes a 2D or 3D computer simulation program which illustrates movement of the body part graphically. In an alternative embodiment, the computer 4 includes a program to translate the detected gesture, posture and movement of the fingers, hand and/or arm into the action of keystrokes or computer mouse command including mouse movement, button clicks, and wheel rolling. This facilitates a virtual computer input device or human-machine interface.

In an alternative embodiment the interface 5 between digital signal processing module 3 and computer 4 is wireless. The transducer 1, ultrasound transmitter and receiver 2, and digital signal processing module 3 are incorporated into a compact unit that can be worn by a person. In yet a further embodiment the compact unit may include a data collection module for storing received signals and/or parameter data. This would enable the wearer to go about their daily activities with the stored data being accessible at a later time for analysis of gesture, posture and movement. This is beneficial for medical analysis and rehabilitation, such as movement and gait analysis.

In another alternative embodiment, the ultrasound transmitter and receiver 2, digital signal processing module 3, and computer 4 are incorporated into a compact unit that can be worn by a person. Such a compact unit can further include transducers to become an all-in-one unit. The transducers can be arranged on the back of a watch-like compact unit, which can be worn on the limb. The compact unit has a communication port that can transfer data with another computer, which can be used during training or downloading stored gesture, posture and movement information for further analysis. In the compact unit, the ultrasound signals can be processed in real-time to obtain the gesture, posture and movement information of the body part. This real-time information can be used for the prosthesis control, control and monitoring for functional electrical stimulation, computer control, robotic control, and capturing gesture language.

Initially, in order to determine the reference information training is required. The various patterns of reflected and scattered ultrasound signal parameters are obtained for different gestures and postures. Movement associated with changes in gesture and posture are analysed and the information is stored in a look-up table. The look-up table can be a simple list of values or a set of coefficients of a sophisticated system modelling like an artificial neural network. During training the apparatus is connected to computer 4 which guides the wearer through various gestures, postures and movements. As knowledge of the correlation between the ultrasound signals from the soft tissues and the corresponding gestures, postures and movements are accumulated for various persons it is envisaged that the training process for individual wearers may be ultimately eliminated.

The training can be performed with a local computer or with a remote computer via networks like the Internet. In the remote mode, the local computer or similar device that connects to the network only provides a data link between the ultrasound detector and the remote computer, and a terminal for local data input and output. The remote computer is a central server that can work with many ultrasound detectors simultaneously. The central server controls the training and performs all the data analysis for extracting reference information. Internet training can reduce the cost for the software maintenance and upgrading.

Flat ultrasound transducers are coupled onto the soft tissue using liquid gels or silicon gels on the skin 8 surface. Film-like transducers can also be used. Adhesive substances or tapes like that used in electromyography (EMG) electrodes is used to attach the transducer onto the skin surface. Multiple transducers, transmitters and receivers can be used to monitor the gesture, posture, and movement of different body parts simultaneously. The flat ultrasound transducers are arranged on a flexible substance. This makes the transducer array easy to attach on body parts with various curvatures. The transducers are arranged as one or two dimensional arrays.

The ultrasound transducer can also be integrated with other types of sensors for monitoring the gesture, posture, and movement of a body part, such as EMG electrodes, gyroscope, and accelerometer. Corresponding signal conditioners for the sensors can be used to collected corresponding signals. These signals can be analyzed together with the ultrasound signals obtained by the ultrasound transducer to provide more precise detection of the gesture, posture, and movement of the corresponding body part.

The ultrasound transducers or a compact unit including the transducer, transmitter, receiver, signal collector, and signal analyser can also be embedded into the body or the prosthesis socket of an artificial body part. Wired or wireless links between the body embedded transducers or the compact unit and the outside control unit can be used to transfer electrical energy, signal, and data. This is particularly useful for people with artificial limbs. The transducers or the compact unit can be embedded into the body during or after the amputation surgery. The method and apparatus can be used to obtain information to mechanically manipulate/move artificial limbs in response to gestures and postures of the remained body parts. The body embedded transducer or compact unit can also be used with body embedded functional electrical stimulation system for controlling or monitoring the gesture, posture, or movement of a body part. For the controlling purpose, the ultrasound transducer will be arranged on the muscle that is used to control the electrical stimulation. For the monitoring purpose, the transducer will be arranged on the muscle to be stimulated.

A tissue stimulator 17 can be used to manipulate the soft tissues including the muscle and tendon of the body part being monitored by the detecting ultrasound signal of the ultrasound system. The tissue stimulator can be a compressor for loading and unloading the tissue in a static way, a vibrator for vibrating the tissue in a low frequency, or a second ultrasound transmitter for transmitting a stimulating ultrasound beam into the tissue.

In an embodiment using a compressor as tissue stimulator 17 the tissue is compressed during the continuous collection of the detecting ultrasound signals. The reflected and/or scattered ultrasound signals collected before and after compression is applied are processed to determine the deformation of the tissue due to the compression. The amount of tissue deformation relates to the stiffness and other mechanical properties of the tissue. Thus, tissue stiffness information can be obtained using this compressing process.

In an embodiment using a vibrator as tissue stimulator 17 the tissue is vibrated during the continuous collection of the detecting ultrasound signals. The reflected and/or scattered ultrasound signals collected during the tissue vibration are processed to obtain the propagation speed of the vibration in the tissue, which relates to the tissue stiffness and other mechanical properties. Thus, tissue stiffness information can be obtained using this vibrating process.

In an embodiment using a second ultrasound transmitter as tissue stimulator 17 the tissue is stimulated and subsequently the detecting ultrasound beam is disturbed. How the reflected and/or scattered ultrasound signals of the detecting ultrasound beam are disturbed by the stimulating ultrasound beam, for example the change of amplitude and central frequency, relates to the tissue stiffness and other mechanical properties. Thus, the tissue stiffness information can be obtained using this stimulating process.

The stiffness of the muscle and tendon relates to the degree of the contraction and stretching, respectively. Since the muscle contraction and tendon stretching further relates to the posture or gesture of the body part, the tissue stiffness information can be used to estimate the posture or gesture using reference information stored during a training process.

Figure 2:
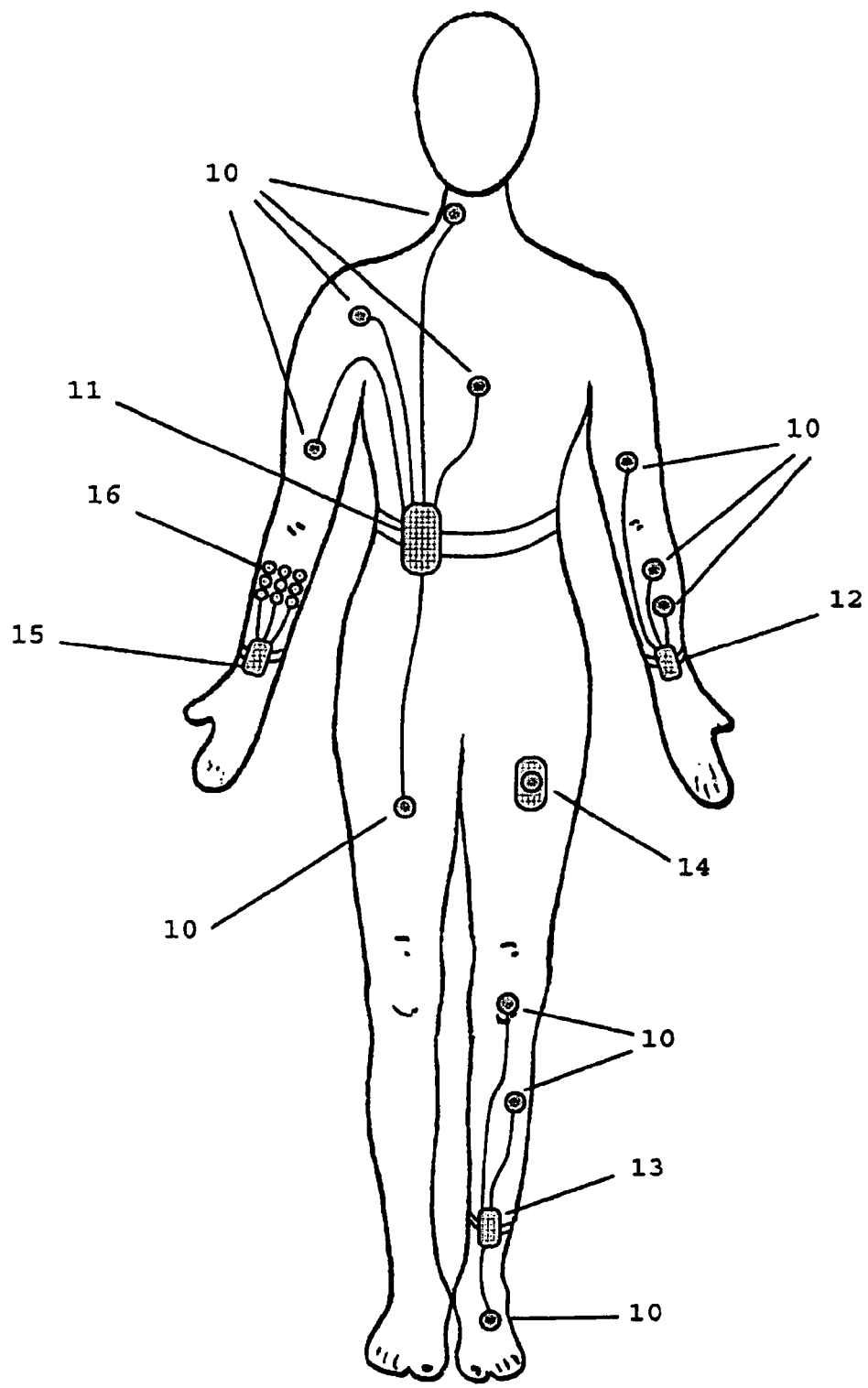
FIG. 2 illustrates the typical locations of transducers and receivers on parts of the body for detecting gesture, posture and movement of respective body parts.

FIG. 2 illustrates some typical locations of transducers and compact receiving units on parts of the body for detecting gesture, posture and movement of respective body parts. Ultrasound transducers 10 are arranged on various parties of the body. A wearable receiving unit 11 is attached on the waist and connects to the transducers 10 that are attached on the neck, chest, shoulder, upper arm, and upper leg. The postures and movements of the head, trunk, upper arm, forearm, and lower leg can be monitored, respectively.

A watch-like receiving unit 12 is worn on the wrist and connects to transducers 10 that are attached on the forearm and upper arm. The gestures and movements of the upper arm, wrist and fingers can be monitored.

A second wearable receiving unit 13 is attached on the lower leg and connects to the transducers 10 that are attached on the knee, lower leg, and foot. The postures and movements of the knee joint, lower leg, foot, and toes can be monitored.

A compact receiving unit 14 integrated with a transducer is attached on the upper leg to monitor the posture and movement of the lower leg.

A second watch-like receiving unit 15 is attached on the wrist and connects to an array of transducers 16 that are attached on the forearm. The gestures and movements of the wrist and individual fingers can be monitored.

FIG. 2 only shows examples of the arrangement of transducers and receiving units on the front of the body, they can also be attached on the sides and back of the body.

A system according to the invention is useful for posture, movement and gait analysis in biomedical engineering and sports. It may also find application in robot controls, virtual reality systems, human-machine interfaces, game controllers and for capturing life-like movements for animated characters.

Where in the foregoing description reference has been made to integers or elements having known equivalents then such are included as if individually set forth herein.

Embodiments of the invention have been described, however it is understood that variations, improvements or modifications can take place without departure from the spirit of the invention or scope of the appended claims.

What is claimed is:

1. A method for indirectly assessing the movement of a musculoskeletal body part of a person including:
    applying an ultrasound transmitter and receiver to a musculoskeletal body part to be monitored, the body part comprising at least one of a head, a neck, a trunk, a shoulder, a chest, a limb, a wrist, a hand, a knee, a foot, a toe, a finger, and an artificial body part,
    using the transmitter to transmit an ultrasound signal into soft tissue of the body part and receiving a reflected and/or scattered ultrasound signal from the soft tissue at the receiver,
    manipulating the reflected and/or scattered ultrasound signal to obtain parameter data, the parameter data comprising at least one of amplitude, phase, flight-time, frequency spectrum and waveform pattern of the signal, and
    comparing the parameter data to reference information to obtain a gesture or posture for the body part and analyzing changes in the gesture or posture to obtain movement information for the body part.

2. A method for indirectly assessing the movement of a musculoskeletal body part of a person including:
    applying an ultrasound transducer or transducer array to a musculoskeletal body part to be monitored, the body part comprising at least one of a head, a neck, a trunk, a shoulder, a chest, a limb, a wrist, a hand, a knee, a foot, a toe, a finger, and an artificial body part,
    using a transmitter to transmit an ultrasound signal into soft tissue of the body part and receiving a reflected and/or scattered ultrasound signal from the soft tissue at the receiver via the ultrasound transducer or transducer array,
    manipulating the reflected and/or scattered ultrasound signal to obtain parameter data, the parameter data comprising at least one of amplitude, phase, flight-time, frequency spectrum and waveform pattern of the signal, and
    comparing the parameter data to reference information to obtain a gesture or posture for the body part and analyzing changes in the gesture or posture to obtain movement information for the body part.

3. A method as claimed in claim 2 wherein the ultrasound signal is transmitted into muscle tissue used to manipulate the body part.

4. A method as claimed in claim 2 wherein the ultrasound signal is transmitted into tendon tissue linking muscle tissue and the body part.

5. A method as claimed in claim 2 including an initial training step for obtaining reference information, the training step including:
    using the transmitter to transmit one or more training signals into the body part and receiving reflected and/or scattered training signals at the receiver via the ultrasound transducer or transducer array,
    manipulating the reflected and/or scattered training signals to obtain training parameter data, wherein the training parameter data includes one or more of amplitude, phase, flight-time, frequency spectrum and waveform pattern of the reflected training signals, and
    storing the training parameter data as reference information.

6. A method for indirectly assessing the movement of a musculoskeletal body part of a person including:
    applying an ultrasound transducer or transducer array to a musculoskeletal body part to be monitored, the body part comprising at least one of a head, a neck, a trunk, a shoulder, a chest, a limb, a wrist, a hand, a knee, a foot, a toe, a finger, and an artificial body part,
    using a transmitter to transmit ultrasound signals into soft tissue of the body part and receiving reflected and/or scattered ultrasound signals from the soft tissue at the receiver,
    manipulating the reflected and/or scattered ultrasound signals to obtain a plurality of parameter data, the parameter data comprising at least one of amplitude, phase, flight-time, frequency spectrum and waveform pattern of the signal, and
    comparing changes in the parameter data to obtain a gesture or posture for the body part and analyzing changes in the gesture or posture to determine movement information for the body part.

7. Apparatus for indirectly assessing the movement of a musculoskeletal body part of a person including:
    an ultrasound transducer or transducer array for attaching to a musculoskeletal body part to be monitored, the body part comprising at least one of a head, a neck, a trunk, a shoulder, a chest, a limb, a wrist, a hand, a knee, a foot, a toe, a finger, and an artificial body part,
    an ultrasound transmitter and receiver for transmitting an ultrasound signal into soft tissue of the body part and receiving a reflected and/or scattered ultrasound signal from the soft tissue,
    a signal processor for manipulating the reflected ultrasound signal to obtain parameter information, the parameter information comprising at least one of amplitude, phase, flight-time, frequency spectrum and waveform pattern of the signal, and
    a processor for storing reference information and comparing the parameter information to said reference information to obtain a gesture or posture for the body part and analyze changes in the gesture or posture to determine movement information for the body part.

8. Apparatus as claimed in claim 7 further including a data collector for receiving and storing the reflected and/or scattered signal and/or parameter information.

9. Apparatus as claimed in claim 7 wherein the ultrasound transmitter is adapted and arranged to transmit the ultrasound signal into muscle tissue, and the receiver is adapted and arranged to receive the reflected and/or scattered ultrasound signals for the muscle tissue via the ultrasound transducer or transducer array.

10. Apparatus as claimed in claim 7 wherein at least the processor is implemented on a computer, the computer including a display to graphically illustrate gesture, posture and/or the movement information for the body part.

11. Apparatus as claimed in claim 7 wherein the ultrasound transducer, transmitter and receiver, signal processor, and the processor are integrated into a compact unit that can be worn on the body part.

12. Apparatus as claimed in claim 7 wherein the ultrasound transducer, transmitter and receiver, signal processor, and the processor are integrated into a compact unit that can be embedded in the body part.

13. Apparatus as claimed in claim 7 wherein the ultrasound transducer is integrated with other types of sensors for monitoring gesture, posture, and/or the movement of the body part.

14. Apparatus as claimed in claim 7 wherein the ultrasound transducer has a flat shape.

15. Apparatus as claimed in claim 7 wherein the ultrasound transducer is attached on the body surface by adhesive materials on the transducer surface.

16. Apparatus as claimed in claim 7 wherein the ultrasound transducer is embedded in the inner surfaces of a prosthesis socket.

17. Apparatus as claimed in claim 7 wherein the ultrasound transducer array is arranged on a flexible substance.

18. A method for indirectly assessing the movement of a body part of a person including:
applying an ultrasound transmitter and receiver to a body part to be monitored, the body part comprising at least one of a head, a neck, a trunk, a shoulder, a chest, a limb, a wrist, a hand, a knee, a foot, a toe, a finger, and an artificial body part,
applying a tissue stimulator on the body part to manipulate muscle and/or tendon tissue of the body part,
using the transmitter to transmit a detecting ultrasound signal into the body part and receiving a reflected and/or scattered ultrasound signal at the receiver,
processing the reflected and/or scattered ultrasound signal to obtain the stiffness information of the muscle and/or tendon tissue, and
comparing the stiffness information to reference information to obtain movement information for the body part.

19. Apparatus for indirectly assessing the movement of a body part of a person including:
an ultrasound transducer or transducer array for attaching to a body part to be monitored, the body part comprising at least one of a head, a neck, a trunk, a shoulder, a chest, a limb, a wrist, a hand, a knee, a foot, a toe, a finger, and an artificial body part,
an ultrasound transmitter and receiver for transmitting a detecting ultrasound signal into the body part and receiving a reflected and/or scattered ultrasound signal,
a tissue stimulator for manipulating muscle and/or tendon tissues of the body part,
a signal processor for processing the reflected ultrasound signal to obtain the tissue stiffness information, and
a processor for storing reference information and comparing the tissue stiffness information to said reference information to determine movement information for the body part.

20. Apparatus as claimed in claim 19 wherein the tissue stimulator is a compressor for loading and unloading the muscle and/or tendon tissues in a static way.

21. Apparatus as claimed in claim 19 wherein the tissue stimulator is a low frequency vibrator for vibrating the muscle and/or tendon tissues.

22. Apparatus as claimed in claim 19 wherein the tissue stimulator is a second ultrasound transmitter for transmitting a stimulating ultrasound beam into the muscle and/or tendon tissues.

* * * * *